United States Patent [19]

Stemmler

[11] Patent Number: 4,598,441
[45] Date of Patent: Jul. 8, 1986

[54] APPARATUS FOR THE MANUFACTURE OF ABSORPTION PADS FOR ABSORBING BODY FLUID

[75] Inventor: Kurt Stemmler, Neuwied, Fed. Rep. of Germany

[73] Assignee: Winkler & Dunnebier Maschinenfabrik und Eisengiesserei GmbH & Co. KG, Neuwied, Fed. Rep. of Germany

[21] Appl. No.: 712,022

[22] Filed: Mar. 15, 1985

[30] Foreign Application Priority Data

Apr. 13, 1984 [DE] Fed. Rep. of Germany ....... 3413925

[51] Int. Cl.⁴ .................... D01G 13/00; D04H 1/00
[52] U.S. Cl. ............................ 19/145; 19/148; 19/302; 425/81.1
[58] Field of Search .............. 156/62.8, 62.4; 425/81.1, 82.1; 19/302, 148, 307, 308, 145, 148, 144; 28/121; 264/112, 113, 510, 511, 517, 571

[56] References Cited

U.S. PATENT DOCUMENTS

| 2,086,757 | 7/1937 | Williams | 425/81.1 |
| 3,201,499 | 8/1965 | Casse | 264/121 |
| 3,628,534 | 12/1971 | Donohue | 128/296 |
| 3,939,240 | 2/1976 | Savich | 28/121 |
| 3,943,605 | 3/1976 | Nystrand | 19/145 |
| 3,952,124 | 4/1976 | Mesek | 156/62.8 |

*Primary Examiner*—Michael Ball
*Attorney, Agent, or Firm*—Collard, Roe & Galgano

[57] ABSTRACT

There is provided an apparatus for the manufacture of absorption pads for absorbing body fluid which is composed of two substantially identical so-called flake applicators each including a vacuum cylinder having shaped recesses which are so-called flake wheels. A first component layer of the absorption pad is produced on the first flake wheel and a second component layer is produced on the second flake wheel. The component layers produced on the first flake wheel are applied to the component layers produced on the second flake wheel by means of a transfer roll. A second transfer roll lifts the finished absorption pad from the second flake wheel and delivers the absorption pad by means of a vacuum belt to a machine for further processing.

6 Claims, 1 Drawing Figure

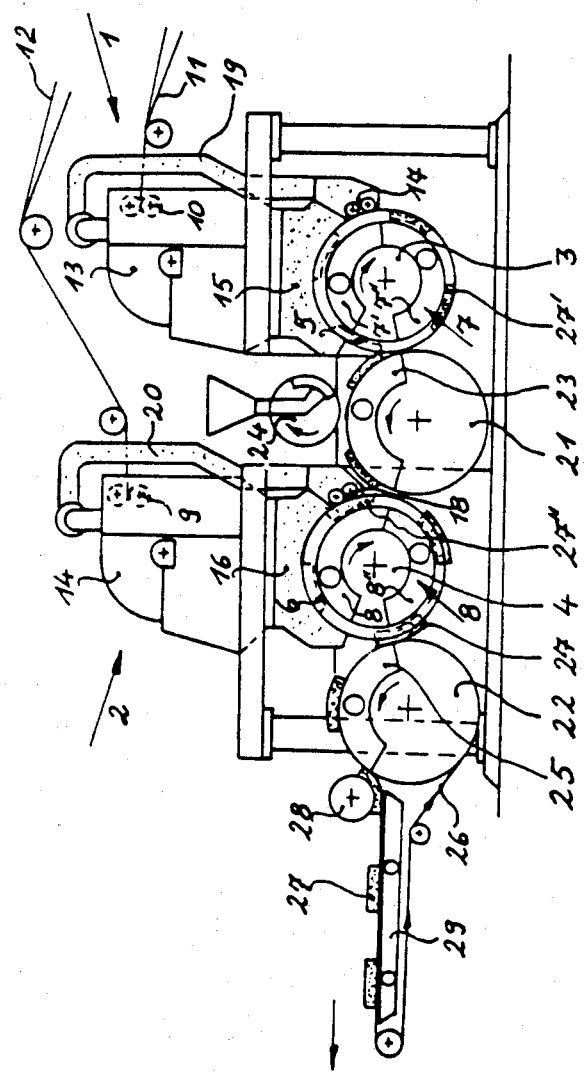

APPARATUS FOR THE MANUFACTURE OF ABSORPTION PADS FOR ABSORBING BODY FLUID

The present invention relates to apparatus for the manufacture of absorbent pads for absorbing body fluids and, more particularly, it relates to an apparatus for producing absorbent pads for sanitary napkins or the like which are shaped to fit the human body.

One of the requirements to be satisfied in the manufacture of absorbent pads for sanitary napkins which absorb body fluids is to provide the pad with a fit or shape conforming to the body of the wearer to thus serve the comfort of the wearer. This requirement is often difficult to meet since it is necessary that the absorption pad have a high absorptivity for body fluids without making the volume of the pad too large or bulky.

This requirement that the absorption pad have a comfortable fit shaped to conform to the human body has been satisfied either by complicated cutting, folding and compressing of a web of flaked material, or by shaping the absorption pads on a rotating vacuum drum, a so-called flake wheel.

Such a flake wheel is basically comprised of a hollow cylinder with vacuum in the interior of the cylinder and with shaped recesses or depressions in its shell for receiving the flaked material. These recesses are provided in the form desired for the finished absorption pads.

The bottoms of these shaped recesses are designed to be permeable to air and thus to communicate with the vacuum in the interior of the flake wheel.

The flaked material, in most cases a cellulose material crushed in suitable mills, is delivered to the surface of the flake wheel by means of a current of air, sucked into the shaped recesses as a result of the vacuum at the bottoms of the recesses to thereby fill said depressions.

The excess amount of flaked material sucked into the recesses is then removed in a subsequent process step, for example by combing with the help of rotating brushes. In this way, an absorption pad is produced which, with respect to shape and size, conforms to the shaped recesses in the shell of the vacuum drum.

Absorption pads so produced always have a flat side, which means that the optimal contour for its purpose of application can be produced only on one side of the pad.

Furthermore, the composition of such absorption pads is largely homogeneous, which means their absorptivity for body fluid is established by the amount of cellulose flakes processed for making the pad.

It is, therefore, a primary object of the present invention to provide apparatus suitable for the manufacture of absorption pads having on all sides of the pad a profile shaped to conform to the human body. It is a further object of the present invention to provide a further development of such apparatus permitting the insertion of a layer of superabsorbent media in said absorption pad.

The above objects, as well as others which will hereinafter become apparent, are accomplished in accordance with the present invention by an apparatus which includes a first flake wheel having shaped recesses for producing a first component layer of the absorption pad, a second flake wheel having shaped recesses for producing a second component layer of the absorption pad, a transfer roll arranged between said flake wheels for lifting off the component layers produced on the first flake wheel and depositing said component layers on the component layers disposed in the shaped recesses of the second flake wheel, and a transfer roll for lifting off and removing from the second flake wheel the absorption pads comprised of the two component layers.

The primary advantage of the apparatus according to the present invention is that the absorption pad can be structured so as to comprise two separately produced and later combined component layers, the result of which permits providing the absorption pad with any desired shape.

Another advantage of the inventive apparatus is that it is possible to fit the absorption pad with an insert disposed between the two component layers which is preferably a superabsorbent medium.

Furthermore, structuring the absorption pad of two component parts has the advantage that said component layers may be composed of different materials. By way of example, in the manufacture of sanitary napkins, the layer in contact with the human body may be made of a soft cellulose material with a high draining capability for body fluid while the outside layer may be composed of a material having a high storage or retention capacity.

Other objects and features of the present invention will become apparent from the following detailed description considered in connection with the accompanying drawing. It is to be understood, however, that the drawing is designed as an illustration only and not as a definition of the limits of the invention.

In the drawing there is shown a schematic side elevational view of the apparatus according to the present invention.

Now turning to the drawing, it can be seen that the apparatus according to the present invention is basically comprised of two identical units, the so-called flake applicators, designated 1 and 2. The core element of each flake applicator 1 and 2 is a flake wheel 3 and 4, respectively. Flake wheels 3 and 4 are designed in the known manner as hollow cylinders having shaped recesses 5 and 6, respectively, provided in their outer shells.

Shaped recesses 5 and 6 are designed as exchangeable units, permitting easy change-over when other sizes or products are to be produced. The bottoms of shaped recesses 5 and 6 are designed as sieves, which, in the manner known, communicate with vacuum sources for conducting air via vacuum boxes 7 and 8, respectively, which are arranged in the interior of flake wheels 3 and 4, respectively, and which control the vacuum lines. The vacuum sources are not shown in the figures. Vacuum boxes 7 and 8 are usefully divided into component sections, designated 7' and 7" and 8' and 8", respectively, because of the long vacuum lines. The division of the vacuum boxes was designed in a way such that sections 7' and 8' are designed for a high throughput of air with much generation of dust, whereas the sections or components 7" and 8" are designed for lower air throughput with less generation of dust. Flake mills 9 and 10 are arranged above flake wheels 3 and 4, respectively, for producing cellulose flakes from endless cellulose webs 11 and 12, respectively. Blowers 13 and 14, respectively, produce air currents, by means of which the cellulose flakes are delivered to the outer shell surfaces of flake wheels 3 and 4, respectively, by way of the large-volume ducts 15 and 16, respectively. Combing devices 17 and 18 are disposed downstream of ducts 15 and 16, respectively, in the direction of rotation of flake wheels 3 and 4 to remove excessive flake material by means of pronged rollers not shown in detail, i.e., excessive flake material sucked in and projecting from shaped recesses 5 and 6, respectively. This excessive material is returned to blowers 13 and 14, respectively, by way of conduits 19 and 20, respectively, for reuse.

Each of the two flake wheels 3 and 4 is associated with a transfer roll 21 and 22, respectively. The function of transfer roll 21 is to remove the cellulose flakes molded in shaped recesses 5 of flake wheel 3 and which form one component layer 27' of absorption pad 27, deliver said cellulose flakes to flake wheel 4, and deposit said flakes or flake pad on the second component layer 27" formed in the shaped recesses 6 of flake wheel 4.

Vacuum, controlled by a vacuum box 23, is used for lifting component layer 27' from shaped recesses 5 of flake wheel 3, holding said component layer on the shell of transfer roll 21, and depositing said layer on component layer 27" contained in shaped recesses 6 of the flake wheel 4.

A spreading unit 24 is mounted above transfer roll 21 and serves to apply powdered or granulated superabsorbent media to component layer 27' of flake pad 27 as said component layer, which is formed on flake wheel 3, passes under said unit.

Second transfer roll 22 is identical with transfer roll 21, and vacuum, controlled by means of vacuum box 25, is admitted to said second roll in the same manner as with transfer roll 21. However, unlike transfer roll 21, transfer roll 22 is looped by a conveyor belt 26 which is permeable to air, said belt serving the purpose of lifting finished absorption pads 27 from shaped recesses 6 of flake wheel 4. Subsequently, on a reversing roll 28, absorption pads 27 are lifted from the shell of transfer roll 22 and delivered to a machine (not shown) for further processing by means of conveyor belt 26 by way of a vacuum box 29.

While only a single embodiment of the present invention has been shown and described, it will be obvious that many changes and modifications may be made thereunto without departing from the spirit and scope of the invention.

What is claimed is:

1. Apparatus for the manufacture of absorption pads for absorbing body fluid, in particular for manufacturing absorption pads for sanitary napkins or the like shaped to fit the human body, said apparatus comprising:
   a first flake wheel having shaped recesses for producing a first component layer of the absorption pad;
   a second flake wheel having shaped recesses for producing a second component layer of the absorption pad;
   a first transfer roll arranged between said first and second flake wheels for lifting off the component layer produced on the first flake wheel and depositing said component layer on the second component layer disposed in the shaped recesses of the second flake wheel; and
   a second transfer roll for removing from said second flake wheel the finished absorption pad consisting of said two component layers.

2. The apparatus as defined in claim 1, wherein said shaped recesses of said first and second flake wheels are designed as exchangeable units.

3. The apparatus as defined in claim 1, wherein vacuum boxes are arranged in said first and second flake wheels, said vacuum boxes being divided into component sections of different vacuum and air throughput.

4. The apparatus as defined in claim 1, which further includes means acting on the component layer produced on said first flake wheel for the application of an intermediate layer, in particular for applying a superabsorbent medium, said means being arranged within the zone of said first transfer roll.

5. The apparatus as defined in claim 4, wherein said intermediate applicator means is comprised of a spreading device.

6. The apparatus as defined in claim 4, wherein said intermediate applicator means is comprised of a device for inserting sheets.

* * * * *